United States Patent [19]

Shorr et al.

[11] Patent Number: 5,225,573
[45] Date of Patent: Jul. 6, 1993

[54] INTERMEDIATES TO TETRABROMOPHTHALIC ANHYDRIDE AND PROCESS THEREFOR

[75] Inventors: Leonard Shorr, Haifa; Michael Peled, Beer-Sheva, both of Israel

[73] Assignee: Bromine Compounds Limited, Beer-Sheva, Israel

[21] Appl. No.: 808,073

[22] Filed: Dec. 10, 1991

Related U.S. Application Data

[63] Continuation of Ser. No. 549,170, Jul. 6, 1990, abandoned.

[51] Int. Cl.$^5$ .......................................... C07D 307/89
[52] U.S. Cl. ..................... 549/246; 549/247; 549/254; 549/256; 549/257
[58] Field of Search ............... 549/246, 247, 254, 256, 549/257

[56] References Cited

U.S. PATENT DOCUMENTS

| | | | |
|---|---|---|---|
| 1,891,843 | 12/1932 | Chaw et al. | 549/246 |
| 1,935,648 | 11/1933 | Mares | 549/246 |
| 1,939,216 | 12/1933 | Kyrides | 549/247 |
| 2,092,795 | 9/1937 | Beckett et al. | 549/246 |
| 2,391,226 | 12/1945 | Clifford et al. | 549/247 |
| 2,680,751 | 6/1954 | Prichard | 549/247 |
| 3,862,145 | 1/1975 | Brennan et al. | 549/247 |
| 3,947,494 | 3/1976 | Kuhlmann | 549/247 |
| 4,560,773 | 12/1985 | Telschow | 549/247 |
| 4,879,387 | 11/1989 | Hara | 549/247 |
| 4,883,899 | 11/1989 | Muramoto et al. | 560/14 |
| 4,904,795 | 2/1990 | Bohen et al. | 548/406 |

FOREIGN PATENT DOCUMENTS

| | | | |
|---|---|---|---|
| 690931 | 7/1964 | Canada | 549/246 |
| 330219 | 8/1989 | European Pat. Off. | 549/246 |
| 334049 | 9/1989 | European Pat. Off. | 549/246 |
| 338215 | 10/1989 | European Pat. Off. | 549/246 |
| 1518647 | 2/1969 | Fed. Rep. of Germany | 549/246 |
| 2250550 | 4/1974 | Fed. Rep. of Germany | 549/247 |
| 8057375 | 4/1983 | Japan | 549/247 |
| 906994 | 2/1982 | U.S.S.R. | 549/247 |

OTHER PUBLICATIONS

Hein et al, Chem. Abst. 81-13281q (1974).
Yanagi et al. Chem. Abst. 81-107205v (1974).
Kuhlmann. Chem Abst 84-179885b (1976).
Susan et al, Chem Abst 92-198024b (1980).
Hsieh et al. CA 95-96366j (1981).
DeLuca, CA 108-139687w (1988).
Kreher et al, CA 109-230709m (1988).
Ushhen et al, CA 112-218050u (1990).
Bohen et al, CA 112-218096p (1990).
Muramoto, CA 112-236014q (1990).
Inada et al, CA 113-79268b (1990).
Bohen et al, CA 113-60675k (1990).
Encyclopedia of Chemical Technology, 3rd edition, vol. 17, pp. 738-746 (1982).
J. Slosar, et al. Chemicky promysl. pp. 206-209 (1985).
Chemical Abstracts, vol. 103, 1) CA 103-1243174.
CA 93-P2405592.
CA 101-1298892.

Primary Examiner—Cecilia Tsang
Attorney, Agent, or Firm—Michael N. Meller

[57] ABSTRACT

Tetrabromophthalic anhydride and the corresponding free acid are propared by oxidizing in the liquid phase a compound of the formula

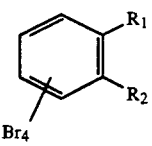

wherein:

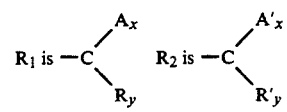

each of A and A' is independently selected from oxygen, OH or acetoxy;
each of R and R' is independently selected from H, OH, alkyl, alkylidene or oxygen;
x is 0 or 1; y is 3 − x; and $R_y$ and $R'_y$ may together form a closed alicyclic or heterocyclic ring structure.

Mixtures of two or more compounds of formula (I), optionally in the presence of an oxidation catalyst, can also be employed as the starting material.

10 Claims, No Drawings

INTERMEDIATES TO TETRABROMOPHTHALIC ANHYDRIDE AND PROCESS THEREFOR

This application is a continuation of application Ser. No. 549,170, filed Jul. 6, 1990 now abandoned.

FIELD OF THE INVENTION

The present invention relates to a process for the preparation of tetrabromophthalic anhydride (TBPA) and to novel intermediates to this product. More specifically, the invention relates to a process in which a brominated precursor of TBPA is oxidized to yield TBPA or a derivative thereof, from which TBPA can be isolated.

BACKGROUND OF THE INVENTION

TBPA is conventionally prepared by brominating phthalic anhydride (PA) in an oleum solution containing 50% or more of free $SO_3$, and using iodine as a catalyst. This process suffers from severe drawbacks: oleum is a hazardous material which is difficult to employ on an industrial scale, because it is corrosive and emits harmful vapors, and it reacts vigorously on contact with moisture. Acidic and toxic gases evolve during the reaction, and the reaction mixture may foam. The bromination reaction is promoted by working at higher temperatures and higher $SO_3$ concentrations, under which condition sulfonation is also promoted, and sulfonated by-products must be removed from the product. Furthermore, iodine is an expensive catalyst, the isolation of the product from the oleum is problematic, and corrosion must be taken into account.

Another process, which suffers from similar drawbacks, brominates PA with bromine and hydrogen peroxide in sulfuric acid, with $I_2$ catalysis [DE-OLS-2 250 550].

Oxidation of tetrabrominated m- and p-xylene has been carried out under specific conditions [U.S. Pat. No. 3,947,494] to obtain phthalic acids of improved quality but with relatively low yields. No oxidation of tetrabrominated o-xylene has been carried out in the art. The much greater difficulty in oxidizing ortho-xylene relative to the other two isomers is clear from the prior art [A.S. Hay et al., J. Org. Chem. 25, 616 (1960)], which teaches that "o-xylene, unlike the other two isomers, cannot readily be oxidized".

SUMMARY OF THE INVENTION

It has now been found, and this is an object of the invention, that it is possible to prepare TBPA by oxidizing a precursor thereof in the presence of a catalyst in the liquid phase. Surprisingly, the process of the invention permits to oxidize compounds such as o-tetrabromoxylene and tetrabromotetralin to obtain TBPA.

By "precursor of TBPA" there is intended a tetrabrominated compound which, when oxidized, gives TBPA or a derivative thereof. Such precursors are, e.g., o-tetrabromoxylene and 5,6,7,8-tetrabromotetralin (TBT). TBT is a novel compound described in a co-pending application of the same applicant, and can be prepared according to the preparation method described below.

DETAILED DESCRIPTION OF THE INVENTION

The process for the preparation of tetrabromophthalic anhydride according to the invention comprises oxidizing in the liquid phase a compound of the formula

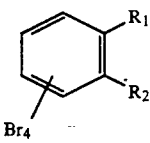

(I)

wherein:

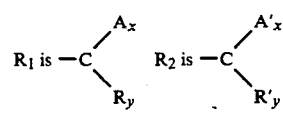

Each of A and A' is independently selected from oxygen, OH or acetoxy;
Each of R and R' is independently selected from H, OH, alkyl, alkylidene or oxygen, with the proviso that at least one of R or R' is H or alkyl;
x is 0 or 1;
y is 3−x, with the proviso that y of R is 1 when A is oxygen, and y of R' is 1 when A' is oxygen;
and wherein $R_y$ and $R'_y$ may together form a closed alicyclic or heterocyclic ring structure;
or a mixture of two or more compounds of formula (I), optionally in the presence of an oxidation catalyst.

Preferably, the oxidizing agent is selected from NaOCl, $NO_2$, $N_2O_4$, $O_2$ and $HNO_3$.

The reaction temperature may be between 30° and 200° C., depending on the specific substrate chosen as well as on the reagent—and the catalyst, if used. For example, if the substrate is a substituted alkyl or carbyl compound and NaOCl is the oxidizing agent, the reaction temperature may be 50° or lower. When unsubstituted o-tetrabromoxylene or TBT are used, with oxygen as oxidant, the temperature may be as high as 200° C.

The oxidation product of the process of the invention may be either the anhydride or the free acid, which dehydrates readily, depending on the conditions applied. Throughout this specification, therefore, whenever the anhydride is referred to this is meant to refer also to the acid, when applicable.

The catalyst can be any material that, in catalytic amounts, promotes the oxidation reaction. Examples of such catalysts are $HNO_3$, CoOAcBr, Se and their mixtures. Other catalysts and catalyst mixture will be recognized by the skilled chemist.

Surprisingly, $HNO_3$ can function both as a catalyst and as part of the reaction solvent. Accordingly, preferred examples of liquid phases comprise those consisting essentially of acetic, sulfuric, perchloric and haloacetic acids, $H_2O$, $HNO_3$ and their mixtures.

In accordance with the present invention there is provided a class of compounds which are novel intermediates for the preparation of tetrabromophthalic anhydride, and which have the formula

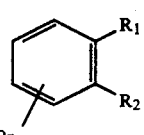

(I)

wherein:

-continued

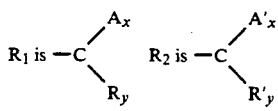

Each of A and A' is independently selected from oxygen, OH or acetoxy;
Each of R and R' is independently selected from H, OH, alkyl, alkylidene or oxygen, with the proviso that at least one of R or R' is H or alkyl;
x is 0 or 1;
y is $3-x$, with the proviso that y of R is 1 when A is oxygen, and y of R' is 1 when A' is oxygen;
and wherein $R_y$ and $R'_y$ may together form a closed alicyclic or heterocyclic ring structure.

Examples of such intermediates are o-tetrabromoxylene, o-tetrabromoxylene-$\alpha,\alpha'$-diol, DTB (1,2-diacetoxymethyl-3,4,5,6-tetrabromobenzene),

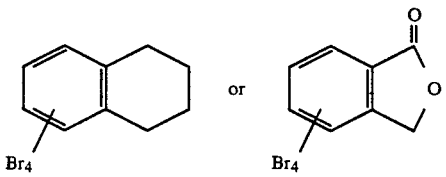

As will be apparent to a person skilled in the art, mixtures of such intermediates may be created by the partial oxidation of one intermediate. For instance, oxidation of the tetrabromoxylene may lead to a mixture of TBPA and tetrabromophthalide. Further oxidation of their mixture will subsequently lead to TBPA as the product.

The above and other characteristics and advantages of the invention will be further understood through the following illustrative and non-limitative examples thereof.

TBT Preparation Method

A) Impurities wash

Tetralin is thoroughly washed several times, e.g., with concentrated H$_2$SO$_4$, in order to remove impurities. Removal of impurities is of paramount importance for obtaining a pure product. However, if Tetralin which has been previously purified is used, or high-grade Tetralin obtained from any other source, then of course this step can be dispensed with.

B) Bromination

To a 1 liter three-necked flask equipped with mechanical stirrer, cooling sleeve and funnel, there are added 79 gr. (0.6 moles) of purified Tetralin from step A, 500 ml methylene dichloride and 2 gr. aluminum chloride as a catalyst. To this mixture there are added dropwise 420 gr. (2.6 moles) of bromine during about one hour. HBr evolves throughout the reaction. After completion of these operations, the resulting mixture is stirred for an additional one hour.

The reaction is carried out at reflux. At the end of the reaction the mixture is cooled, bleached with ammonia or bisulfite, neutralized with a 10% diluted carbonate solution, filtered and washed with water. The solvent is then evaporated, and 214 gr. of a solid product is obtained, having a melting point of 180° C. The yield is 80% with respect to Tetralin.

The solid is recrystallized from ethyl acetate, to provide a white to off white solid with a m.p. of 184°–186° C., which is soluble in chloroform, and is not soluble in alcohols, acetone, acetonitrile or petrol ether 6080. Recrystallization can likewise be carried out using THF, dioxane, toluene, xylene, etc.
N.M.R. (CDCl$_3$): 1.8 (M, 4H), 2.7 (M, 4H).
I.R. (KBr): 830, 950, 1300, 1360, 1420, 2900
Br %-calculated: 71.4, found: 72.2
Sublimation point: 160° C./1 mmHg

EXAMPLE 1

Oxidation of p-Tetrabromoxylene-$\alpha,\alpha'$-diol

To a 1 lit. 3-necked flask with mechanical stirrer, a cooler, temperature control and thermostatic bath, there were added 500 ml of concentrated nitric acid, and the temperature was raised to 90°–95° C., at which point addition of tetrabromoxylene diol began. The reagent was added in 5–10 gr portions, one every 10–15 minutes, to a final added weight of 62.5 gr. Brown gases evolve throughout the reaction. After all the reagent had been added, heating was continued for additional 4–6 hours, until evolution of gases almost stopped.

The reaction mixture was then cooled and filtered, and the filtrate washed with water and dried to give 59.8 gr. (90% yield) of product, with a melting point of 258° C. Further treatment of this product was effected either by recrystallization from xylene to give a purified TBPA, m.p.=268°–270° C., or by further reaction as in Example 6 below.

EXAMPLE 2

Oxidation of 1,2-diacetoxymethyl-3,4,5,6-tetrabromobenzene

Operating as in Example 1, 30 gr. of DTB were added to the nitric acid, to yield 21.9 gr of product (m.p. 257°–260° C.). The product was contaminated with tetrabromophthalide, as previously discussed with respect to Example 1.

EXAMPLE 3

OXIDATION OF o-TBX WITH HNO$_3$ o-TBX (2.12 g., 5 mmol.) was slurried in a mixture of 68% HNO$_3$ (10 ml., 108 mmol.) and HOAc (10 ml.) contained in a 100 ml. Carius tube fitted with a pressure gauge, safety valve (set to 7 atm.), bursting disk (ca. 10 atm.) and inlet tap. The slurry was stirred magnetically. The Carius tube was then pressurised with O$_2$ to 2.1 atm. (five pressurisations with release of gas followed by a final pressurisation to the stated pressue) and placed in an oil-bath maintained at 165° C. The pressure rose to 5 atm. over 0.5 hour and copious brown fumes filled the reaction vessel. At this point the pressure was released and set at 2 atm. After another 1.5 hours the pressure had again reached 5 atm., at which point it was again released and set to 2 atm. Within another 15 mins. the pressure now peaked at 7 atm. The pressure was released and the reaction mixture was allowed to cool. The brownish solution crystallised on cooling. The cold crystallised reaction mixture was poured into water (ca. 200 ml.) and the precipitate was collected by filtration and air-dried to leave an off-white solid (2 g.), whose GLC analysis (area %) indicated the presence of o-TBX (6%), TBPA (46%) and the phthalide (33%). On digestion of this solid in 30 ml. 2.5% NaOH at ca. 40° C., followed by filtration, a clear solution was obtained. This solution was acidified with HCl to give a creamy white precipitate which was collected by filtration and air dried to leave a white solid (1.6 g.) whose GLC spectrum (area %) showed the presence of TBPA (71%) (which appears in the chromatogram as the anhydride) and tetrabromophthalide (28%). Redigestion in NaOH and reprecipitation with HCl yielded pure TBPA of m.p. 265° C. and a neutralization equivalent of 239.7.

Retention times of the analysed compounds are shown in Table I below.

EXAMPLE 4

Oxidation of o-TBX with $O_2$ using $HNO_3$ in under-stoichiometric amounts;

o-TBX (2.26 g., 5.4 mmol.) was slurried in a mixture of HOAc (10 ml.) and 68% $HNO_3$ (2 ml., 21.5 mmol.) using the equipment described above. The initial $O_2$ pressure was set at 3.3 atm. and the Carius tube was immersed in a bath maintained at 166°–170° C. The pressure rose to 4.2 atm. over 30 mins. The pressure then rose again reaching 4.8 atm. after another 120 mins., at which point the pressure was released and the reactor was allowed to cool. On cooling, the pale brown solution crystallised. The cooled reaction mixture was then treated as previously described to yield a white solid (2 g.) whose GLC (area %) showed the presence of o-TBX (1.7%), TBPA (61%) and tetrabromophthalide (25%). Redigestion and reprecipitation as in Example 3 yielded the pure acid, m.p. 265° C., neutralization equivalent 240 and containing 66% Br.

EXAMPLE 5

Oxidation of o-TBX with $O_2$ catalysed by $HNO_3$/Se o-TBX (2.19 g., 5.2 mmol.) was slurried in a mixture of HOAc (10 ml.) containing 68% $HNO_3$ (0.2 ml., 2.2 mmol.) and ca. 5 mg. Se powder. The initial $O_2$ pressure was set at 4.2 atm. and the Carius tube was immersed in an oil bath maintained at 166°–170° C. The pressure rose to 5 atm. over 25 mins. and then slowly fell to 3.4 atm. over another 150 mins. At this point the reactor was cooled, bled of gas, repressurised to 4.2 atm. with fresh $O_2$ and reheated in the oil bath at the above temperature for another 240 mins. The pressure rose to 5.2 atm. The solution was allowed to cool overnight and the resulting slurry was poured into 200 ml. water, filtered and air dried to leave an off-white solid (1.8 g.) whose GLC (area %) showed the presence of o-TBX (1.6%), TBPA (52.5%), tetrabromophthalide (28.6%), 3-acetoxytetrabromophthalide (2.4%) and DTB (2.6%).

EXAMPLE 6

Oxidation of a mixture of TBPA and tetrabromophthalide with NaOCl

A starting mixture containing about 60% TBPA and 40% tetrabromophthalide was digested in 100 ml. 1.4% NaOH solution by heating to 50° C. The hot solution was filtered to leave 130 mg. of insoluble material. To the clear filtrate was added 15 ml. commercial bleach (3% active chlorine) and the mixture was heated for 10 hours during which time another 45 ml. of the bleach was added in three batches. The cooled solution was then acidified with HCl and the white precipitate was collected by filtration and air dried to leave a white solid (4 g.) containing (GLC, area %) 84% TBPA and 14% tetrabromophthalide. When the oxidation was conducted for 24 hours, the product obtained was essentially pure TBPA (neutralization equivalent 240).

EXAMPLE 7

Oxidation of o-TBX with $O_2$ using a CoOAcBr catalyst

The catalyst solution was prepared by dissolution of Co $(OAc)_2.4H_2O$ (5 g., 20 mmol.), $Mn(OAc)_2.4H_2O$ (1.3 g., 5 mmol.) and NaBr (5.2 g., 50 mmol.) in 250 ml. of HOAc. The catalyst contained 0.08 mmol. Co/ml. o-TBX (2.12 g., 5 mmol.) was slurried in a mixture of acetic acid (15 ml.) and the catalyst solution (2 ml., 0.16 mmol. Co). The reactor (Carius tube) was pressurised to 4.2 atm. with $O_2$ and heated to 165° C. The pressure fell to 2 atm. over 60 min. and so the reactor was re-pressurised to 4 atm. and re-heated. The reaction mixture was cooled and the slurry was poured into 200 ml. of water, filtered and the solid was air dried to leave a beige solid (2 g.) containing (GLC, area %) TBPA (50.2%), tetrabromophthalide (23.9%), 3-acetoxytetrabromophthalide (4.2%) and DTB (15.0%).

EXAMPLE 8

Preparation of Tetrabromophthalic Anhydride from Tetrabromotetralin

A stainless-steel pressure bottle was charged with tetrabromotetralin (2.1 g., 4.68 mmol.), acetic acid (10 ml.) and 68% $HNO_3$ (1 ml., 10.8 mmol.). The bottle was flushed with $O_2$, pressurised with $O_2$ to 11 atm. and heated with stirring at 154° C. for 4.5 hours. During the reaction period, the reactor was periodically repressurised to 11 atm. as the $O_2$ reacted with the substrate. On completion of the reaction, the reactor was cooled to room temperature and the reaction mixture was dispersed in 200 ml. cold water. The white precipitate was collected by filtration, washed with water and dried to leave an off-white solid (2.0 g.) whose GLC showed the presence of tetrabromophthalic anhydride (7.4 mins., 52% area). The remainder consisted of partial oxidation products. Pure TBPA was recovered by dissolution of this product in aqueous NaOH, extracting the nonacidic components with ether and reprecipitation with HCl. Upon evaporation of this product to dryness at elevated temperature, there was obtained pure TBPA, as the anhydride, of m.p. 279° C. (reported: 280° C.), containing 68.5% Br (calcd: 69.0%).

EXAMPLE 9

Oxidation of o-TBX with Oxygen in the Presence of a Mixture of $NO_2$ and $N_2O_4$ To a solution of $N_2O_4$ (0.5 g, 7.9 mmol of an equilibrium mixture of $NO_2$ and $N_2O_4$) in 10 ml of 1,2,4-trichlorobenzene there were added 2.1 g (5 mmol) of o-TBX, and the vessel was pressurized to 11 atm. with oxygen.

After three hours at 173° C., the mixture was cooled and the product was precipitated by the addition of hexane. The off-white product was collected by filtration and examined by GC-MS, which showed complete conversion of o-TBX to the phthalic anhydride derivative.

TABLE I

| Analytical Procedures | | |
|---|---|---|
| RENTENTION TIMES: | o-TBX | 5.2 mins. |
| | TBPA (anhydride) | 7.4 |
| | tetrabromophthalide | 7.8 |
| | 3-acetoxytetrabromophthalide | 9.1 |

TABLE I-continued

| Analytical Procedures | |
|---|---|
| DTB | 9.5 |

GLC: HP 5890 connected to a HP 3329A integrator. N₂ as carrier gas.
COLUMN: HP 530μ, fused glass capillary containing methyl silicone as liquid phase.
PROGRAM: 150-0.5 min-10°/min-250-4 min.

We claim:

1. A process for the preparation of tetrabromophthalic anhydride or the corresponding free acid, comprising oxidizing in the liquid phase a compound of the formula

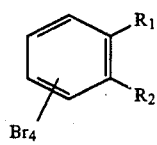

wherein:

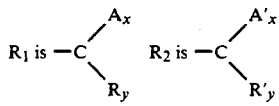

Each of A and A' is independently selected from oxygen, OH or acetoxy;

Each of R and R' is independently selected from H, OH, alkyl, alkylidene or oxygen, with the proviso that at least one of R or R' is H or alkyl and with the further proviso that A and R cannot simultaneously be oxygen;

x is 0 or 1;

y is 3−x, with the proviso that y of R is 1 when A is oxygen, and y of R' is 1 when A' is oxygen;

and wherein $R_y$ and $R'_y$ may together form a closed alicyclic or heterocyclic ring structure of up to 6 carbon atoms wherein oxygen is the hereto atom; or a mixture of two or more compounds of formula (I), optionally in the presence of an oxidation catalyst.

2. A process according to claim 1, wherein the oxidizing agent is selected from the group consisting of NaOCl, NO₂, N₂O₄, O₂ and HNO₃.

3. A process according to claim 2, wherein the catalyst is selected from the group consisting essentially of HNO₃, CoOAcBr, Se, NO₂, N₂O₄ and their mixtures.

4. A process according to claim 2, wherein the liquid phase consists essentially of acetic, sulfuric, perchloric and haloacetic acids, H₂O, HNO₃ and their mixtures.

5. A process according to claim 1, wherein the compound of formula I is selected from the group consisting of o-tetrabromoxylene, o-tetrabromoxylene-α,α'-diol, 1,2-diacetoxymethyl-3,4,5,6-tetrabromobenzene, 5,6,7,8-tetrabromotetralin and tetrabromophthalide.

6. A process according to claim 3, wherein the liquid phase consists essentially of acetic, sulfuric, perchloric and haloacetic acids, H₂O, HNO₃ and their mixtures.

7. A process according to claim 2, wherein the compound of formula I is selected from the group consisting of o-tetrabromoxylene, o-tetrabromoxylene-α,α'-diol, 1,2-diacetoxymethyl-3,4,5-6-tetrabromobenzene, 5,6,7,8-tetrabromotetralin and tetrabromophthalide.

8. A process according to claim 3, wherein the compound of formula I is selected from the group consisting of o-tetrabromoxylene, o-tetrabromoxylene-α,α'-diol, 1,2-diacetoxymethyl-3,4,5-6-tetrabromobenzene, 5,6,7,8-tetrabromotetralin and tetrabromophthalide.

9. A process according to claim 4, wherein the compound of formula I is selected from the group consisting of o-tetrabromoxylene, o-tetrabromoxylene-α,α'-diol, 1,2-diacetoxymethyl-3,4,5-6-tetrabromobenzene, 5,6,7,8-tetrabromotetralin and tetrabromophthalide.

10. An intermediate for the preparation of tetrabromophthalic anhydride, selected from the group consisting of o-tetrabromoxylene-α,α'-diol, 1,2-diacetoxymethyl-3,4,5,6-tetrabromobenzene, 5,6,7,8-tetrabromotetralin and tetrabromophthalide.

* * * * *